(12) United States Patent
Wu et al.

(10) Patent No.: US 6,855,530 B2
(45) Date of Patent: Feb. 15, 2005

(54) HUMAN RNASE H1 MUTANTS

(75) Inventors: Hongjiang Wu, Carlsbad, CA (US);
Walter F. Lima, San Diego, CA (US);
Stanley T. Crooke, Carlsbad, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 119 days.

(21) Appl. No.: 09/992,738

(22) Filed: Nov. 14, 2001

(65) Prior Publication Data

US 2002/0160486 A1 Oct. 31, 2002

Related U.S. Application Data

(60) Provisional application No. 60/248,950, filed on Nov. 15, 2000.

(51) Int. Cl.$^7$ ................................ C12N 9/22
(52) U.S. Cl. ................................ 435/199
(58) Field of Search ........................ 435/199

(56) References Cited

PUBLICATIONS

Bambara et al., "Enzymes and Reactions at the Eukaryotic DNA Replication Fork", J. Biol. Chem. 1997 272(8):4647–4650.

Blyn et al., "Poly (rC) binding protein 2 binds to stem–loop IV of the poliovirus RNA 5' noncoding region: Identification by automated liquid chromatography–tandem mass spectrometry", Proc. Natl. Acad. Sci. USA 1996 93:11115–11120.

Büsen et al., "Ribonuclease H Levels during the Response of Bovine Lymphocytes to Concanavalin A", Eur. J. Biochem. 1977 74:203–208.

Büsen et al., "Purification, Subunit Structure, and Serological Analysis of Calf Thymus Ribonuclease H I*", J. Biol. Chem. 1980 255(19): 9434–9443.

Cerritelli et al., "The non–RNase H domain of Saccharomyces cerevisiae RNase H1 binds double–stranded RNA: Magnesium modulates the switch between double–stranded RNA binding and RNase H activity", RNA 1995 1:246–259.

Cerritelli et al., "Cloning, Expression, and Mapping of Ribonucleases H of Human and Mouse Related to Bacterial RNase HI", Genomics 1998 53:300–307.

Crouch et al., "Ribonucleases H", Nucleases 1985 211–241.

Dabora et al., "Structure of the Acid State of Escherichia coli Ribonucleic HI", Biochemistry 1996 35:11951–11958.

Eder et al., "Ribonuclease H from K562 Human Erythroleukemia Cells", J. Biol. Chem. 1991 266(10): 6472–6479.

Eder et al., "Substrate specificity of human RNASE H1 and its role in excision repair of ribose residues misincorporated in DNA", Biochimie 1993 75:123–126.

Frank et al., "Cloning of the cDNA encoding the large subunit of human RNase HI, homologue of the prokaryotic RNase HII", Proc. Natl. Acad. Sci. USA 1998 95:12872–12877.

Frank et al., "Purification and characterization of human ribonuclease HII", Nucleic Acids Research 1994 22(24):5247–5254.

Hirata et al., "The Phosphorylation and DNA Binding of the DNA–binding Domain of the Orphan Nuclear Receptor NGFI–B", J. Biol. Chem. 1993 268(33):24808–24812.

Itaya et al., "Molecular cloning of a ribonuclease H (RNase HI) gene from an extreme thermophile Thermus thermophilus HB8–a thermostable RNase H can functionally replace the Escherichia coli enzyme in vivo", Nucleic Acids Research 1991 19(16):4443–4449.

(List continued on next page.)

Primary Examiner—Charles L. Patterson, Jr.
(74) Attorney, Agent, or Firm—Licata & Tyrrell P.C.

(57) ABSTRACT

A human RNase H polypeptide and methods of use are provided.

5 Claims, 4 Drawing Sheets

OTHER PUBLICATIONS

Itaya et al., "Selective cloning of genes encoding RNase H from *Salmonella typhimurium, Saccharomyces cerevisiae* and *Escherichia coli* rnh mutant", Mol. Gen. Genet 1991 227:438–445.

Kanaya et al., "Importance of the Positive Charge Cluster in *Escherichia coli* Ribonuclease HI for the Effective Binding of the Substrate", J. Biol. Chem. 1991 266(18): 11621–11627.

Kanaya et al., "Expression, Purification, and Characterization of a Recombinant Ribonuclease H from Thermus thermophilus HB8", J. Biol. Chem. 1992 267(14):10184–10192.

Katayanagi et al., "Crystal Structure of *Escherichia coli* RNase HI in Complex With Mg2+ at 2.8Å Resolution:Proof for a Single Mg2 Binding Site", Proteins: Structure, Function and Genetics 1993 17:337–346.

Katayanagi et al., "Three–dimensional structure of ribonuclease H from *E. coli*", Nature 1990 347:306–309.

Landt et al., "A general method for rapid site–directed mutagenesis using the polymerase chain reaction", Gene 1990 96:125–128.

Lima et al., "Binding Affinity and Specificity of *Escherichia coli* RNASE H1:Impact on the Kinetics of Catalysis of Antisense Oligonucleotide–RNA Hybrids", Biochemistry 1997 36:390–398.

Nakamura et al., "How does RNase H recognize a DNA–RNA hybrid?", Proc. Natl. Acad. Sci. USA 1991 88:11535–11539.

Rong et al., "On the Molecular Weight and Subunit Composition of Calf Thymus", Biochemistry 1990 29(2):383–389.

Sambrook J., Fritsch E.F. and Maniatis T. In Molecular Cloning. A Laboratory Manual, 2nd ed. Cold Spring Harbor Laboratory Press, Cold Spring Harbor, NY 1990 18.47–18–59 and A.1–A.3.

Scaringe et al., "Novel RNA Synthesis Method Using 5'–O–Silyl–2'–0–orthoester Protecting Groups", J. Am. Chem. Soc. 1998 120:11820–11821.

Stein et al., "Enzyme from Calf Thymus Degrading, the RNA Moiety of DNA–RNA Hybrids: Effect on DNA–Dependent RNA Polymerase", Science 1969 166:393–395.

Turchi et al., "Enzymatic completion of mammalian lagging–strand DNA replication", Proc. Natl. Acad. Sci. USA 1994 91:9803–9807.

Wu et al., "Molecular Cloning and Expression of cDNA for Human RNase H", Antisense & Nucleic Acid Drug Development 1998 8:53–61.

Wu et al., "Properties of Cloned and Expressed Human RNASE H1", J. Biol. Chem. 1999 274(40):29280–28278.

Yang et al., "Structure of Ribonuclease H Phased at 2 Å Resolution by MAD Analysis of the Selenomethionyl Protein", Science 1990 249:1398–1405.

HUMAN RNASE H1 MUTANTS

This application claims the benefit of provisional application 60/248,950, filed Nov. 15, 2000.

INTRODUCTION

RNase H hydrolyzes RNA in RNA-DNA hybrids (1). RNase H activity appears to be ubiquitous in eukaryotes and bacteria (2–7). Although RNase H's constitute a family of proteins of varying molecular weight, the nucleolytic activity and substrate requirements appear to be similar for the various isotypes. For example, all RNase H's studied to date function as endonucleases exhibiting limited sequence specificity and requiring divalent cations (e.g., $Mg^{2+}$, $Mn^{2+}$) to produce cleavage products with 5' phosphate and 3' hydroxyl termini (8).

Two classes of RNase H enzymes have been identified in mammalian cells (5, 9–10). These enzymes were shown to differ with respect to co-factor requirements and were shown to be inhibited by sulfhydryl reagents (10–11). Although the biological roles of the mammalian enzymes are not fully understood, it has been suggested that mammalian RNase H1 may be involved in replication and that the RNase H2 enzyme may be involved in transcription (12–13).

Recently, both human RNase H genes have been cloned and expressed (11, 14–15). RNase H1 is a 286 amino acid protein with a calculated mass of 32 kDa (11). The enzyme is encoded by a single gene that is at least 10 kb in length and is expressed ubiquitously in human cells and tissues. The amino acid sequence of human RNase H1 displays strong homology with RNase H1 from yeast, chicken, E. coli and the mouse (11). The human RNase H2 enzyme is a 299 amino acid protein with a calculated mass of 33.4 kDa and has also been shown to be ubiquitously expressed in human cells and tissues (14, H. Wu, unpublished data). Human RNase H2 shares strong amino acid sequence homology with RNase H2 from C. elegans, yeast and E. coli (14).

The properties of the cloned and expressed human RNase H1 have recently been characterized (16). The activity of RNase H1 is $Mg^{+2}$ dependent and inhibited by both $Mn^{+2}$ and the sulfhydryl blocking agent N-ethylmaleimide. Human RNase H1 was also inhibited by increasing ionic strength with optimal activity for both KCl and NaCl observed at 10–20 mM. The enzyme exhibited a bell-shaped response to divalent cations and pH, with the optimum conditions for catalysis observed to be 1 mM $Mg^{2+}$ and pH 7–8. The protein was shown to be reversibly denatured under the influence of temperature and destabilizing agents such as urea. Renaturation of human RNase H1 was observed to be highly cooperative and did not require divalent cations. Furthermore, RNase H1 displayed no tendency to form intermolecular disulfides or to form homomultimers. Human RNase H1 was shown to bind selectively to "A-form" duplexes with 10–20-fold greater affinity than that observed for E. coli RNase H1 (16–17). Finally, human RNase H1 displays a strong positional preference for cleavage, i.e., the enzyme cleaves between 8 and 12 nucleotides from the 5'-RNA-3'-DNA terminus of the duplex.

Many of the properties observed for Human RNase H1 are consistent with the E. coli RNase H1 isotype, (e.g., the cofactor requirements, substrate specificity and binding specificity) H1 (16–17). In fact, the carboxy-terminal portion of human RNase H1 is highly conserved with the amino acid sequence of the E. coli enzyme, (region III, FIG. 1). The glutamic acid and two aspartic acid residues of the catalytic site, as well as the histidine and aspartic acid residues of the proposed second divalent cation binding site of the E. coli enzyme are conserved in human RNase H1 (18–21). In addition, the lysine residues within the highly basic α-helical substrate-binding region of E. coli RNase H1 are also conserved in the human enzyme.

Despite these similarities, the structures of the two enzymes differ in several important ways. For example, the amino acid sequence of the human enzyme is approximately 2-fold larger than the E. coli enzyme. The additional amino acid sequence of the human enzyme extends from the amino-terminus of the conserved E. coli RNase H1 region and contains a 73 amino acid region homologous with a double-strand RNA (dsRNA) binding motif, (region I, FIG. 1). The conserved E. coli RNase H1 region at the carboxy-terminus is separated from the dsRNA-binding domain of the human enzyme, by a 62 amino acid region, (region II, FIG. 1). Although the role of both regions I and II remain unclear, the dsRNA-binding domain of human RNase H1may account for the observed positional preference for cleavage displayed by the enzyme as well as the enhanced binding affinity of the enzyme for various polynucleotides (16).

Figure 1:
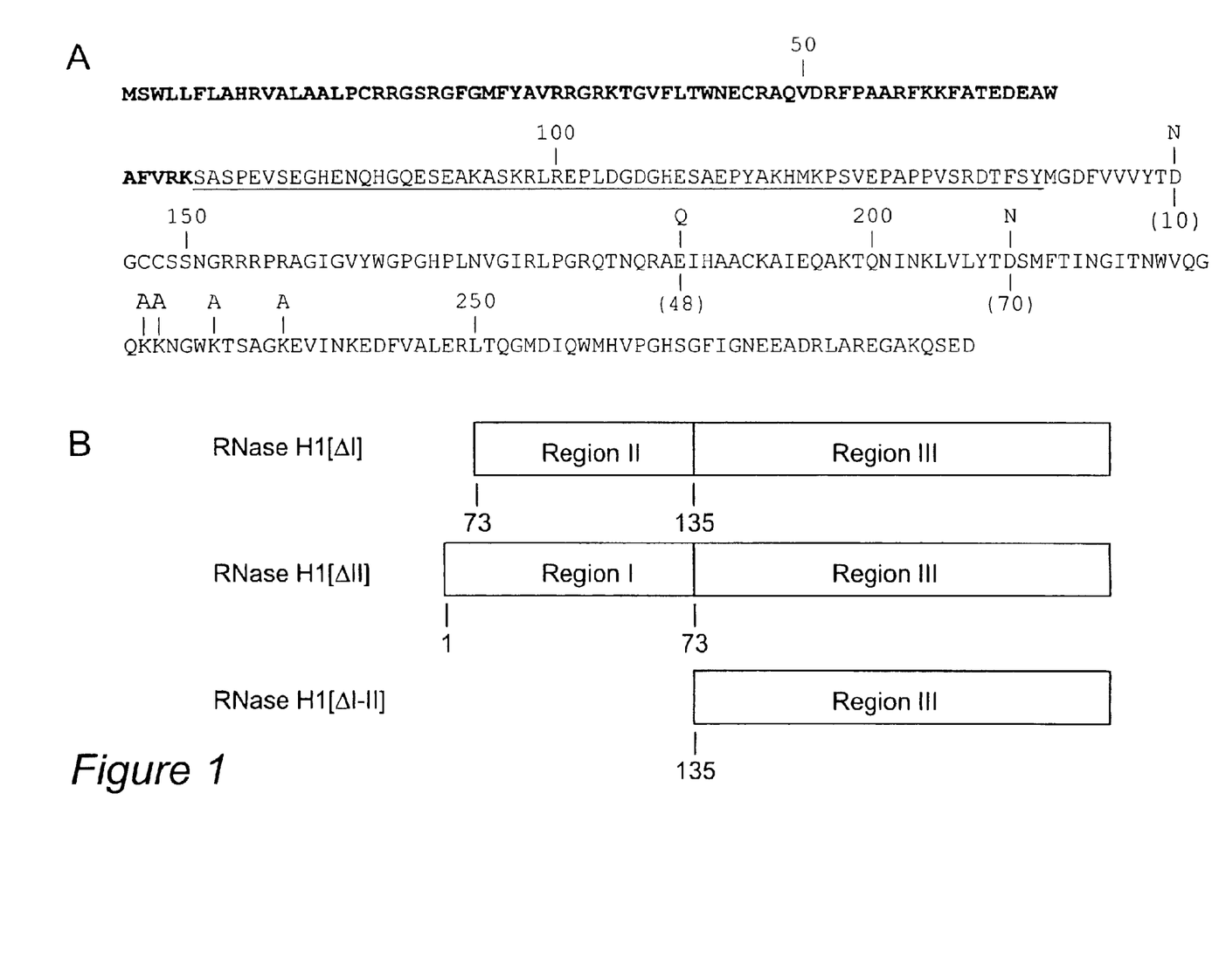

In this study we have explored the roles of the conserved amino acids of the catalytic site and the basic substrate-binding domain (region III), the roles of the dsRNA-binding domain (region I) and the 62 amino acid center region of human RNase H1 (region II), (FIG. 1). We have performed site-directed mutagenesis on the three conserved amino acids of the proposed catalytic site of human RNase H1 ([D145N], [E186Q], and [D210N]). In addition, the net positive charge of the basic substrate-binding domain was progressively reduced through alanine substitution of two (RNase H1[K226, 227A]) and four (RNase H1[K226,227, 231,236A]) of the lysines within this region. Deletion mutants were also prepared in which either the dsRNA-binding domain of region I (RNase H1[ΔI]), or the central region II (RNase H1[ΔII]) was deleted. Finally, a mutant protein representing the conserved E. coli RNase H1 region was prepared by deleting both region I and II, (RNase H1[ΔI–II]).

SUMMARY OF INVENTION

The carboxy-terminus of human RNase H1 (SEQ ID NO:3) is highly conserved with E. coli RNase H1 (SEQ ID NO:1) and contains the amino acid residues of the putative catalytic site and basic substrate-binding domain of the E. coli RNase enzyme. The amino-terminus of human RNase H1 contains a structure consistent with a double-strand RNA (dsRNA) binding motif that is separated from the conserved E. coli RNase H1 region of the carboxy-terminus by a 62 amino acid sequence. We have performed site-directed mutagenesis on human RNase H1. These studies showed that although the conserved amino acid residues of the putative catalytic site and basic substrate-binding domain are required for RNase H activity, deletion of either the catalytic site or the basic substrate-binding domain did not ablate binding to the heteroduplex substrate. Deletion of the region between the dsRNA-binding domain and the conserved E. coli RNase H1 domain resulted in a significant loss in the RNase H activity. Furthermore, this deletion mutant competitively inhibited the cleavage activity of the wild-type enzyme suggesting that this central 62 amino acid region does not contribute significantly to the binding affinity of the enzyme for the substrate. The dsRNA-binding domain was not required for RNase H1 activity, as the dsRNA-deletion mutants exhibited cleavage rates comparable to the rate observed for wild-type enzyme. Comparison of the dissociation constant of human RNase H1 and the RNase H1[ΔI–II] mutant for the heteroduplex substrate suggested that the greatest contribution to binding is from the region situated within the conserved E. coli RNase H1 region of human RNase H1. Finally, comparison of the cleavage patterns exhibited by the mutant proteins with the cleavage pattern for the wild-type enzyme indicates that the dsRNA-binding domain is responsible for the observed strong positional preference for cleavage exhibited by human RNase H1.

FIGURE LEGENDS

FIG. 1. Schematic showing the structure of the human RNase H1 mutant proteins SEQ ID NO: 3. (A) Position of amino acid substitution mutants. Mutants include: asparagine substitution of aspartic acid at position 145 [D145N], glutamine substitution of glutamic acid at position 186 [E186Q], asparagine substitution of Aspartic acid at position 210 [D210N], alanine substitution of lysine at positions 226 and 227 [K226, 227A], and alanine substitution of lysine at positions 226, 227, 231 and 236 [K226, 227, 231, 236A]. The amino acids of regions I, II and III are represented by, respectively, in bold, underlined and plain lettering. Designations within parentheses indicate amino acid positions of E. coli RNase H1. (B) Description of deletion mutants of human RNase H1. RNase H1[ΔI] corresponds to the deletion of region I (amino acid positions 1–73), RNase H1[ΔII] corresponds to the deletion of region II (amino acid positions 74–135) and RNase H1[ΔII–II] corresponds to the deletion of regions I and II (amino acid positions 1–135).

MATERIALS AND METHODS
Construction of Mutant Proteins

The mutagenesis of human RNase H1 was preformed using a PCR-based technique derived from Landt, et al. (22). Briefly, two separate PCR were performed using a set of site-directed mutagenic primers and two vector-specific primers (11). Approximately 1 μg of human RNase H1 cDNA was used as the template for the first round of amplification of both the amino- and carboxy-terminal portions of the cDNA corresponding to the mutant site. The fragments were purified by agarose gel extraction (Qiagen, Germany). PCR was preformed in two rounds consisting of, respectively, 15 and 25 amplification cycles (94° C., 30 s; 55° C., 30 s; 72° C., 180 s). The purified fragments were used as the template for the second round of PCR using the two vector-specific primers. The final PCR product was purified and cloned into the expression vector pET17b (Novagen, Wis.) as described previously (11). The incorporation of the desired mutations was confirmed by DNA sequencing.

Protein Expression and Purification

The plasmid was transfected into E. coli BL21(DE3) (Novagen, Wis.). The bacteria were grown in M9ZB medium (24) at 32° C. and harvested at $OD_{600}$ of 0.8. The cells were induced with 0.5 mM IPTG at 32° C. for 2 h. The cells are lysed in 8M urea solution and the recombinant protein was partially purified with Ni-NTA agarose (Qiagen, Germany).

The human RNase H1 was purified by C4 reverse phase chromatography (Beckman, System Gold, Fullerton, Calif.) using a 0% to 80% gradient of acetonitrile in 0.1% trifluoroacetic acid/distilled water (% v/v) over 40 min (25). The recombinant protein was collected, lyophilized and analyzed by 12% SDS-PAGE (24). The purified protein and control samples were re-suspended in 6 M urea solution containing 20 mM Tris-HCl, pH 7.4, 400 mM NaCl, 20% glycerol, 0.2 mM Phenylmethylsulfonyl fluoride (PMSF), 5 mM dithiothreitol (DTT), 10 μg/ml each aprotinin and leupeptin (Sigma, Mo). The protein was refolded by dialysis with decreasing urea concentration from 6 M to 0.5 M and DTT concentration from 5 mM to 0.5 mM (25). The refolded protein was concentrated 10-fold using a Centricon apparatus (Amicon, Mass.).

Synthesis of Oligonucleotides

The oligoribonucleotides were synthesized on a PE-ABI 380B synthesizer using 5'-O-silyl-2'-O-bis(2-acetoxyethoxy)methyl ribonucleoside phosphoramidites and procedures described elsewhere (23). The oligoribonucleotides were purified by reverse-phase HPLC. The DNA oligonucleotides were synthesized on a PE-ABI 380B automated DNA synthesizer and standard phosphoramidite chemistry. The DNA oligonucleotides were purified by precipitation 2 times out of 0.5 M NaCl with 2.5 volumes of ethyl alcohol.

Preparation of $^{32}$P Labeled Substrate

The RNA substrate is 5'-end-labeled with $^{32}$P using 20 u of T4 polynucleotide kinase (Promega, Wis.), 120 pmol (7000 Ci/mmol) [γ-$^{32}$P]ATP (ICN, CA) , 40 pmol RNA, 70 mM tris, pH 7.6, 10 mM $MgCl_2$ and 50 mM DTT. The kinase reaction is incubated at 37° C. for 30 min. The labeled oligoribonucleotide was purified by electrophoresis on a 12% denaturing polyacrylamide gel (24). The specific activity of the labeled oligonucleotide is approximately 3000 to 8000 cpm/fmol.

Preparation of the Heteroduplex

The heteroduplex substrate was prepared in 100 μL containing 50 nM unlabeled oligoribonucleotide, $10^5$ cpm of $^{32}$P labeled oligoribonucleotide, 100 nM complementary oligodeoxynucleotide and hybridization buffer [20 mM tris, pH 7.5, 20 mM KCl]. Reactions were heated at 90° C. for 5 min, cooled to 37° C. and 60 u of Prime RNase Inhibitor (5 Prime →3 Prime, CO) and $MgCl_2$ at a final concentration of 1 mM were added. Hybridization reactions were incubated 2–16 h at 37° C. and β-mercaptoethanol (BME) was added at final concentration of 20 mM.

Determination of Initial Rates ($V_o$)

The heteroduplex substrate was digested with 0.5 ng human RNase H1 at 37° C. A 10 μl aliquot of the cleavage reaction was removed at time points ranging from 2–120 min and quenched by adding 5 μL of stop solution (8 M urea and 120 mM EDTA). The aliquots were heated at 90° C. for two min, resolved in a 12% denaturing polyacrylamide gel and the substrate and product bands were quantitated on a Molecular Dynamics PhosphorImager. The concentration of the converted product was plotted as a function of time. The initial cleavage rate was obtained from the slope (mole RNA cleaved/min) of the best-fit line for the linear portion of the plot, which comprises, in general <10% of the total reaction and data from at least five time points.

Competition experiments were performed as described for the determination of initial rates with the exception that 20 nM oligodeoxynucleatide, 10 nM oligoribonucleotide and 2.5 ng of the mutant RNase H1 protein. Reactions were digested with 250 pg of wild-type Human RNase H. The reactions were quenched, analyzed and quantitated as described for the determination of initial rates.

Determination of Dissociation Constants ($K_d$)

Binding affinities were determined by inhibition analysis (17). The RNA-DNA heteroduplex was prepared as described above except in a final volume of 60 μL and with the concentration of the heteroduplex ranging from 10 nM to 500 nM. The non-cleavable heteroduplex substrate was prepared in 60 μL of hybridization buffer containing equimolar concentrations of oligodeoxynucleotide and complementary 2'-fluoro modified oligonucleotide in excess of the RNA-DNA hybrid. The DNA-2'-flouro duplex was added to the RNA-DNA duplex and the combined reaction was digested with human RNase H1 as described for the determination of initial rates. The reactions were quenched, analyzed and quantitated as described for the determination of initial rates.

Results

Figure 2:
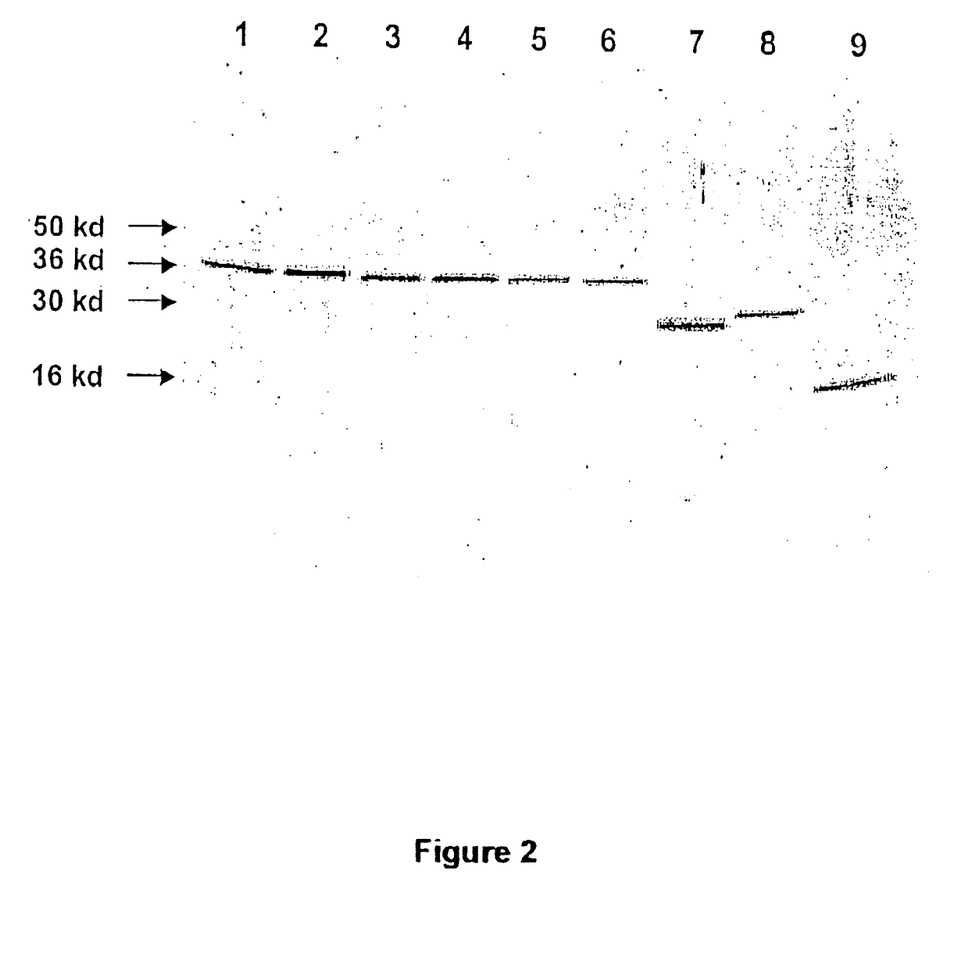
FIG. 2. SDS-polyacrylamide gel analysis of wild-type and mutant human RNase H1 proteins. The purified proteins were separated on a 4–20% gradient Tris-Glycine gel. The human RNase H1 mutants are described in FIG. 1. The human RNase H1 proteins (lanes 1–9) are as follows: wild-type, [D145N], [E186Q], [D210N], [K226, 227A], [K226,227,231,236A], [ΔII], [ΔI] and [ΔI–II].

The mutant proteins of human RNase H1 prepared for this study are described in FIG. 1. Analysis of human RNase H1 and the mutant proteins by SDS-polyacrylamide gel electrophoresis is shown in FIG. 2. As expected, mutant proteins containing amino acid substitutions, (e.g., D145N, E186Q, D210N, K226,227A and K226,227,231,236A) exhibited molecular weights similar to the 32 kDa wild-type enzyme (lanes 1–6). The RNase H1[ΔI] mutant in which the dsRNA-binding domain was deleted resulted in a 213 amino acid protein with an approximate molecular weight of 23 kDa (lane 7). The deletion of the 62 amino acid center portion of human RNase H1 (RNase H1[ΔII]) resulted in a 224 amino acid protein with an approximate molecular weight of 25 kDa (lane 8). Finally, the deletion of both the dsRNA-binding domain and the central region of the enzyme (RNase H1[ΔI–II]) resulted in a 151 amino acid protein containing the conserved *E. coli* RNase H1 sequence and with an approximate molecular weight of 17 kDa (lane 9).

The initial cleavage rates ($V_o$) were determined for the human RNase H1 enzyme and the mutant proteins using a 17 nucleotide long RNA/DNA heteroduplex, (Table 1).

TABLE I

Initial cleavage rates for wild-type and mutant human RNase H1 proteins. Initial cleavage rates were determined as described in Materials and Methods. The initial cleavage rates are an average of n ≧ 3 measurements.

| Human RNase H1 Protein | $V_o$ (pM min$^{-1}$)* |
|---|---|
| Wild-type Rnase H1 | 658 ± 130 |
| RNase H1 [D145N] | below detection limit |
| RNase H1 [E186Q] | below detection limit |
| RNase H1 [D210N] | below detection limit |
| RNase H1K226, 227A] | 8.1 ± 0.2 |
| RNase H1K226, 227, 231, 236A] | below detection limit |
| RNase H1 [ΔI] | 488 ± 38 |
| RNase H1 [ΔII] | 11 ± 2 |
| RNase H1 [ΔI–II] | 610 ± 20 |

*Detection limit = cleavage rates resulting in <1% of the heteroduplex substrate over 60 min.

Substitution of any one the three amino acids comprising the proposed catalytic site of human RNase H1, (e.g., [D145N], [E186Q], and [D210N]) ablated the cleavage activity of the enzyme. The RNase H1[K226,227A] mutant exhibited an initial cleavage rate almost two orders of magnitude slower than the rate observed for the wild-type enzyme. The alanine substitution of two remaining lysine residues within the basic substrate binding domain (RNase H1[K226,227,231,236A]) resulted in cleavage activity below the detection limit of the assay.

The initial cleavage rate for the RNase H1[ΔI] mutant in which the dsRNA-binding domain was deleted was 30% slower than the initial cleavage rate observed for the wild-type enzyme (Table 1). The deletion of region II of human RNase H1 resulted in an even greater reduction in the cleavage rate. In this case, the initial cleavage rate observed for the wild-type enzyme was approximately 60-fold faster than the rate observed for the RNase H1[ΔII] mutant. Conversely, the initial cleavage rate for the mutant protein in which both regions I and II were deleted (RNase H1[ΔI–II]) was comparable to the initial cleavage rate observed for the wild-type enzyme.

Figure 3:
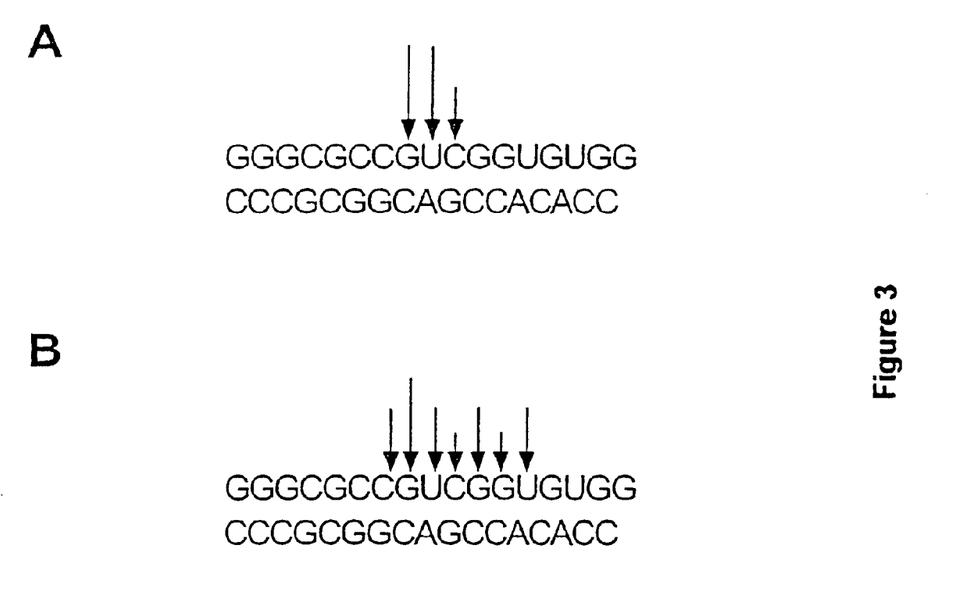
FIG. 3. RNase H Cleavage site for wild-type and mutant proteins on the 17-mer RNA-DNA heteroduplex. Digestion of the heteroduplex was preformed as described in Materials and Methods. The RNA sequence (5'→3') (SEQ ID NO:2) is shown above the DNA sequence (SEQ ID NO:4). The arrows indicate the sites of enzymatic digestion, and the size of the arrows reflect the relative cleavage intensities. (A) Cleavage pattern for wild-type RNase H1, RNase H1[ΔII] and RNase H1[K226, 227A] proteins. (B) Cleavage pattern for RNase H1[ΔI] and [ΔI–II] mutants.

The positions of the cleavage sites for the wild-type and mutants of human RNase H1 in the heteroduplex substrate are shown in FIG. 3. As previously observed, human RNase H1 exhibited a strong positional preference, i.e., 8 to 12 nucleotides from the 5'-RNA/3'-DNA terminus of the duplex (FIG. 3A). A similar cleavage pattern was observed for both the RNase H1[K226,227A] substitution mutant and the RNase H1[ΔII] deletion mutant. The RNase H1[ΔI] and H1[ΔI–II] deletion mutants exhibited broader cleavage patterns on the heteroduplex substrate, with cleavage sites ranging from 7 to 13 nucleotides from the 5'-terminus of the RNA (FIG. 3B).

Figure 4:
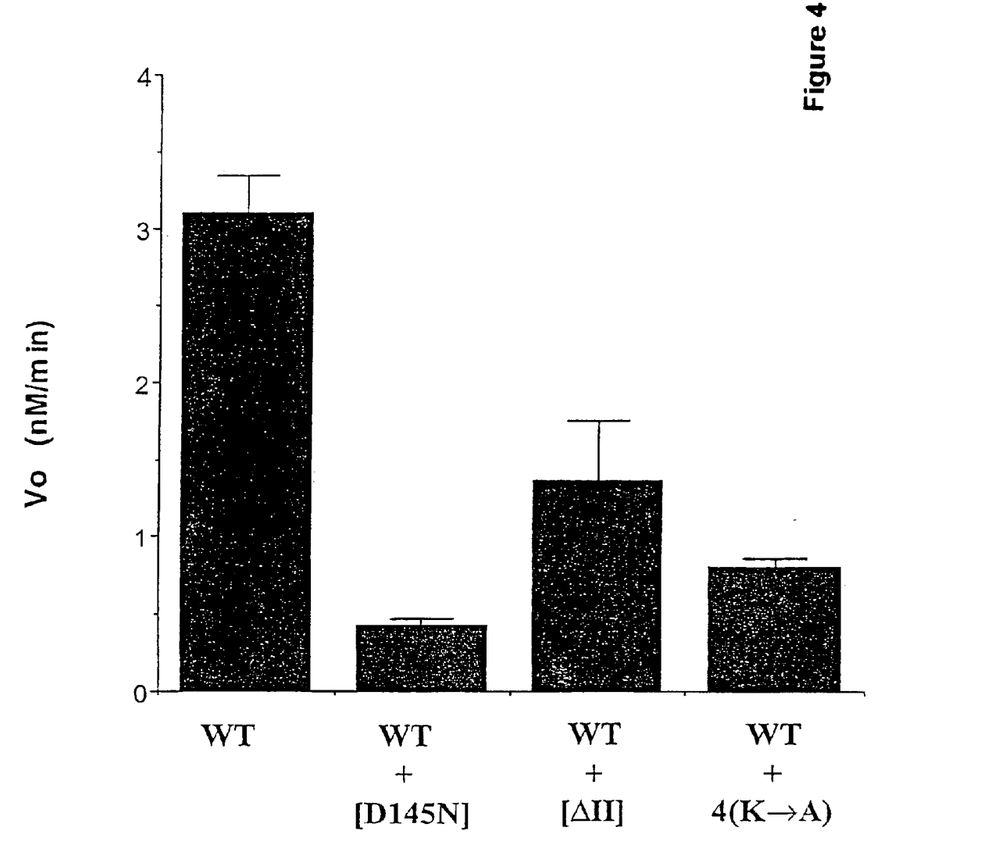
FIG. 4. Competitive inhibition of wild-type human RNase H1 activity by mutant proteins. Competition experiments were performed as described in Materials and Methods. The heteroduplex substrate was incubated with the mutant proteins prior to adding the wild-type RNase H1 enzyme. The concentration of the wild-type human RNase H1 enzyme was in excess of the substrate concentration. The concentration of the mutant proteins was 10-fold in excess of the wild-type enzyme. The initial rate for the wild-type human RNase H1 enzyme alone and in the presence of the RNase H1[D145N], [ΔII] and [K226,227,231,236A] (4×K→A) mutants was determined as described in Materials and Methods.

Experiments were performed to determine whether the inactive mutants of human RNase H1 competitively inhibit the cleavage activity of the wild-type enzyme. These experiments were performed with the enzyme concentration in excess of the substrate concentration and with the concentration of the mutant protein in excess of the wild-type enzyme concentration. All three of the mutant proteins tested were observed to competitively inhibit the cleavage activity of human RNase H1 (FIG. 4). For example, the initial cleavage rate of human RNase H1 alone was determined to be 6-fold faster than the initial cleavage rate for human RNase H1 in the presence of the RNase H1[D145N] mutant. The initial cleavage rate of human RNase H1 in the presence of the region II deletion mutant (RNase H1[ΔII]) was approximately 50% slower than the rate observed for human RNase H1 alone. Finally, the initial cleavage rate for human RNase H1 in the presence of the RNase H1[K226, 227,231,236A] mutant was approximately 60% slower than the rate observed for human RNase H1 alone.

The binding affinities of human RNase H1 and the RNase H1[ΔI–II] mutant were determined indirectly using a competition assay as previously described (17). Briefly, the cleavage rate of the RNA/DNA heteroduplex was determined at a variety of substrate concentrations in both the presence and absence competing noncleavable DNA/2'F heteroduplex. The dissociation constant ($K_d$) of human RNase H1 for the DNA/2'F heteroduplex was 75 nM. The RNase H1[ΔI–II] mutant exhibited a $K_d$ of 126 nM for the DNA/2'F heteroduplex (Table II).

TABLE II

Binding Constants of RNase H1 proteins.
$K_d$ measurements were determined as described in Materials and Methods. The $K_d$ value for E. coli RNase H1 was derived from previously reported data (17). The dissociation constants for human RNase H1 proteins are derived from ≧2 slopes of Lineweaver-Burk analysis.

| RNase H1 Protein | $K_d$(nM) |
|---|---|
| Human RNase H1 [ΔI–II] | 75 ± 8 |
| Human RNase H1 [ΔI–II] | 125 ± 22 |
| E. coli RNase H1 | 1600 |

Discussion

Structure of Human RNase H1

The human RNase H1 protein can be divided into three regions (FIG. 1). Region I, located at the amino-terminus of the enzyme, contains a structure consistent with a dsRNA-binding motif. Region II consists of a 62 amino acid region between the dsRNA-binding domain and the conserved E. coli RNase H1 region. Lastly, region III is situated at the carboxy-terminus of human RNase H1 and contains an amino acid sequence that is highly conserved with the amino acid sequence of E. coli RNase H1. Included within region III are the conserved amino acid residues that form the putative catalytic site, the second divalent cation binding site, and the basic substrate-binding domain of the E. coli enzyme.

Catalytic Triad

The three amino acids (Asp-10, Glu-48 and Asp-70) that make up the catalytic site of E. coli RNase H1 were identified by site-directed mutagenesis (20). These amino acid residues have also been shown to be involved with the coordination of the requisite divalent cation cofactor, (25). Comparison of the amino acid sequence of E. coli RNase H1 with the amino acid sequences of the RNase H domain of retroviruses and RNase H1 from yeast, chicken, Human and mouse indicates that these three amino acid residues are conserved among all type 1 sequences (11).

Mutant proteins of human RNase H1 were prepared in which each of the three conserved catalytic residues Asp-145, Glu-186 and Asp-210 was substituted with, respectively, Asn, Gln and Asn. The complete ablation of cleavage activity observed for the RNase H1[D145N], [E186Q] and [D210N] mutants indicates that all three of the conserved residues in human RNase H1 are required for catalytic activity (Table 1). The fact that the RNase H1[D145N] mutant competitively inhibited the activity of human RNase H1 suggests that the loss in cleavage activity observed for this mutant protein was not due to a loss in the binding affinity for the heteroduplex substrate (FIG. 4). Taken together these data suggest that, consistent with the E. coli enzyme, the three conserved residues likely form the catalytic site of the enzyme and are not involved in the substrate-binding interaction.

Basic Substrate Binding Domain

The amino acid sequence of the basic substrate-binding region of E. coli RNase H1 is highly conserved in the human enzyme (11). The basic substrate-binding domain of E. coli RNase H1 has been extensively characterized and has been shown to comprise the α-helix III and following loop region of the enzyme (18, 20–21). The crystal structure of E. coli RNase H1 indicates that this region forms a relatively independent sub-domain with the loop region composed of a cluster of basic amino acid residues. These basic amino acid residues are believed to bind electrostatically to the phosphate backbone of the heteroduplex substrate.

Mutant proteins of human RNase H1 were prepared to determine whether these conserved basic amino acids served a similar function in the human enzyme. The RNase H1[K226,227A] mutant, in which two lysine residues were substituted with alanine residues, exhibited a cleavage rate two orders of magintude slower than the wild-type human enzyme (Table 1). The alanine substitution of all four lysine residues within the putative substrate-binding domain of human RNase H1 (RNase H1[K226,227,231,236A]) resulted in the complete loss of RNase H activity. Furthermore, the RNase H1[K226,227,231,236A] mutant was shown to competitively inhibit the cleavage activity of wild-type human enzyme (FIG. 4), suggesting that the observed loss of RNase H activity for the mutant protein was not due to a loss in the overall binding affinity of the mutant protein for the substrate.

The properties observed for basic amino acid residues of human RNase H1 differ significantly from those observed for the E. coli enzyme. First, unlike the human enzyme the alanine substitution of any two of the basic residues within the substrate-binding domain of E. coli RNase H1 did not affect the cleavage activity of the mutant E. coli proteins, i.e., the cleavage rates for the alanine substituted mutants were comparable to the rates observed for the wild-type E. coli enzyme (18). Second, alanine substitution of four basic amino acids within the substrate-binding domain of E. coli RNase H1 resulted in a 5–10-fold reduction but not the ablation of the RNase H activity of the E. coli mutants. In addition, a 30 to 60-fold increase in the $K_m$ was observed. for these mutant proteins suggesting that a reduction in the binding affinity for the substrate was responsible for the observed reduction in cleavage activity. In the case of human RNase H1 mutant, the complete loss in cleavage activity for the RNase H1[K226,227,231,236A] mutant did not coincide with a loss in binding affinity for the substrate.

Clearly, these conserved basic residues appear to perform different functions within the two RNase H1 enzymes. Whether these substituents are interacting directly with the substrate is not clear, but the fact that the alanine substitution of the conserved lysine residues resulted in the reduction and/or ablation of the RNase H activity indicates that these residues are essential for the catalytic processes of the human enzyme. In contrast to the human enzyme, the basic residues of the E. coli enzyme appear to be the key substituents that make up the binding surface of the protein. Furthermore, alanine-scanning mutagenesis of the basic residues of the substrate-binding domain of E. coli RNase H1 suggested that the binding interaction has more to do with the net positive charge of the basic amino acid cluster than on specific interactions involving specific basic amino acid residues of the E. coli enzyme (18). Finally, our data also suggest that other regions within human RNase H1 are contributing to the binding affinity of the enzyme. One likely region that may be involved in substrate binding is the dsRNA-binding domain of the human enzyme.

Region I

Human RNase H1 has been observed to contain the canonical α-β-β-β-α structure consistent with the dsRNA-binding motif (11). The position of the double-strand RNA binding domain at the amino-terminus of the enzyme is consistent with the structure observed for RNase H1 from *Saccharomyces cerevisiae* (26). The human RNase H1 dsRNA-binding domain differs from the yeast enzyme in that the human sequence appeared to correspond to a more complete dsRNA-binding motif. The properties of the dsRNA-binding domain of human RNase H1 were also observed to differ from the yeast enzyme in that the dsRNA-binding domain of the human enzyme was not modulated by divalent cation concentration. For example, RNase H1 from *Saccharomyces cerevisiae* was observed to bind to dsRNA at $Mg^{2+}$ concentrations below those required to activate the enzyme and was inhibited from binding to dsRNA at $Mg^{2+}$ concentrations that activated the enzyme. In other words, binding to dsRNA and the RNase H activity of the *Saccharomyces cerevisiae* enzyme were observed to be mutually exclusive. Contrary to the yeast enzyme, the binding of human RNase H1 to dsRNA was determined not to be affected by $Mg^{2+}$ concentrations required to activate the enzyme.

Deletion mutants of human RNase H1 were prepared in order to investigate the role of the dsRNA-binding domain, i.e. region I. These mutants included the deletion of the dsRNA-binding domain (RNase H1[ΔI]) and deletion of both the dsRNA-binding domain and region II between the dsRNA-binding domain and the conserved *E. coli* RNase H1 region (RNase H1[ΔI–II]). Both mutants in which the dsRNA-binding domain was deleted cleaved the heteroduplex substrate at a rate comparable to the rate observed for the wild-type enzyme (Table I). A mutant of RNase H1 from *Saccharomyces cerevisiae* in which the dsRNA-binding domain was deleted also exhibited RNase H activity (26). In light of the fact that the RNase H activity and dsRNA-binding properties of the yeast enzyme are mutually exclusive, it is not surprising that the yeast enzyme would remain active with the dsRNA-binding domain deleted. On the other hand, the robust cleavage activity of the human deletion mutants is surprising, particularly when considering that the RNase H1[K226,227,231,236A] mutant was able to bind to the heteroduplex substrate. The cleavage activity of the RNase H1[ΔI] and [ΔI–II] mutants suggests that the enzyme does not require the dsRNA-binding domain in order to bind to the heteroduplex substrate. In fact, the binding affinity of the wild-type human enzyme for the heteroduplex substrate was <2-fold tighter than the RNase H1[ΔI–II] mutant without the dsRNA-binding domain (Table II). Clearly both the basic substrate-binding domain and the dsRNA-binding domain contribute to the overall binding affinity of human RNase H1 as the elimination of either domain did not affect the ability of the enzyme to bind to the substrate. It is important to note that these human RNase H1 proteins are His-tag fusion proteins and it is possible that the binding properties of the proteins may be enhanced by the His-tag. Numerous studies have shown that a His-tag does not interfere with nucleic acid binding properties as it is very small (few amino acids), and its pK is near neutral (27–28). The cleavage pattern for the mutants in which the dsRNA-binding region was deleted (RNase H1[I] and [I–II]) differed from the pattern observed for the wild-type human enzyme. In fact the cleavage pattern for the RNase H1[I] and [I–II] mutants resembled the cleavage pattern of the *E. coli* RNase H1 enzyme which does not contain a dsRNA-binding domain. Taken together these data suggest that the dsRNA-binding domain is responsible for the observed strong positional preference for cleavage exhibited by human RNase H1, (16) and further suggest that this region contributes to the overall binding affinity of the enzyme for the substrate and the regulation of the sites of cleavage. Finally, the broad cleavage pattern observed for the RNase H1[I–II] mutant further suggests that the strong positional preference for cleavage displayed by human RNase H1 is not responsible for slower cleavage rate of the human enzyme compared to *E. coli* RNase H1. The cleavage rate observed for human RNase H1 was approximately two orders of magnitude slower than the rate observed for the *E. coli* enzyme (17). The strong positional preference for cleavage displayed by human RNase H1 in effect limits the number of productive binding interactions for a given substrate. Considering that RNase H1[I–II] mutant displayed a similar cleavage pattern to the *E. coli* enzyme, the slower cleavage rate observed for human RNase H1 is likely not due to the strong positional preference for cleavage.

The role of the dsRNA-binding domain is not clear. Obviously the dsRNA-binding domain of human RNase H1 is not required for RNase H activity and consequently this region likely serves another function. RNase H1 enzymes have been proposed to participate in DNA replication and are believed to aid in the removal of the RNA primers during the DNA replication of the lagging strand. The strong positional preference for cleavage exhibited by the human RNase H1 proteins containing the dsRNA-binding domain is consistent with the average length of the RNA primers which have been shown to range from 7–14 nucleotides (29). Therefore the role of the dsRNA-binding domain of human RNase H1 may be to place the enzyme in the appropriate position on the RNA primer in order to ensure efficient removal of the primer.

Region II

Region II comprises the amino acid sequence between the dsRNA-binding domain (region I) and the conserved *E. coli* RNase H1 domain (region III). Deletion of this region (RNase H1[II]) resulted in a significant loss in the cleavage activity when compared to the wild-type enzyme. The RNase H1[II] mutant was also shown to competitively inhibit the cleavage activity of human RNase H1 suggesting that the loss in RNase H activity did not appear to be due to a reduction in the binding affinity of the RNase H1[II] mutant for the heteroduplex substrate. Consequently, one possibility for the loss in RNase H activity observed for the RNase H1[ΔII] mutant may be due to the misfolding of the enzyme into an inactive conformation as a result of deleting region II. Alternatively, deletion of region II places the dsRNA-binding domain immediately adjacent to the conserved *E. coli* RNase H1 region of the human enzyme which may result in steric hindrance of the catalytic site by the dsRNA-binding domain.

The loss of cleavage activity observed for the RNase H1[II] mutant is consistent with that observed for RNase H1 of *Trypanosoma brucei* in which the deletion of this region also resulted in the loss of enzymatic activity (A. Campbell, personal communication). Furthermore, this region in the *T. brucei* enzyme has been shown to contain numerous acidic residues and site-directed mutagenesis of the acidic amino acids within this region also resulted in the ablation of the enzymatic activity. The highly acidic nature of this region is consistent in the human enzyme and is found in RNase H1 proteins of *Crithidia fasciculata*, *Drosophila melanogaster* and *Saccharomyces cervisiae*. It is unclear how these acidic residues contribute to the enzymatic activity of human RNase H1, but this region appears to play a critical role in the structure of the enzyme. Clearly, understanding the role of this region with respect to the enzymatic activity of human RNase H1 warrants further investigation.

Region III

Region III, as represented by the H1[I–II] mutant, contains the conserved *E. coli* RNase H1 domain. The cleavage rate observed for the H1[I–II] mutant was comparable to the rate observed for wild-type human enzyme (Table I), but approximately two-orders of magnitude slower than the cleavage rate observed for *E. coli* RNase H1 (17). The robust activity of the RNase H1[I–II] mutant indicates that region III is capable of folding into an active structure independent of regions I and II and further suggests that region III constitutes an autonomous sub-domain of the human enzyme. Folding of the *E. coli* RNase H1 enzyme has been shown to follow a two-step process involving a core folding intermediate (28). The amino acid sequence of the core folding intermediate is highly conserved in the human enzyme, which shares 41% amino acid identity with the *E. coli* enzyme, and suggests a similar folding pathway for human RNase H1[I–II] mutant. Whether the wild-type human enzyme follows a similar folding pathway remains to be determined.

The binding affinity of the RNase H1[I–II] mutant for the heteroduplex substrate was determined to be approximately 10-fold tighter than the binding affinity observed for the *E. coli* enzyme (Table II). Furthermore, the binding affinity of the wild-type human enzyme was <2-fold tighter than that observed for the RNase H1[I–II] mutant. Taken together, these data suggest that region III is providing a significant contribution to the increased binding affinity observed for human RNase H1. The tighter binding affinity observed for both the wild-type and human RNase H1[I–II] mutant likely limits the turnover rate of the human enzyme and may account for the two orders of magnitude slower cleavage rate of the human proteins compared to *E. coli* RNase H1 (17).

References

1. Stein, H. and Hausen, P. (1969) *Science* 166, 393–395
2. Itaya, M. and Kondo, K. (1991) *Nucleic Acids Res.* 19, 4443–4449
3. Itaya, M., McKelvin, D., Chatterjie, S. K., and Crouch, R. J. (1991) *Mol. Gen. Genet.* 227, 438–445
4. Kanaya, S., and Itaya, M. (1992) *J. Biol. Chem.* 267, 10184–10192
5. Busen, W. (1980) *J. Biol. Chem.* 255, 9434–9443
6. Rong, Y. W. and Carl, P. L. (1990) *Biochemistry* 29, 383–389
7. Eder, P. S., Walder, R. T., and Walder, J. A. (1993) *Biochimie* 75, 123–126
8. Crouch, R. J. and Dirksen, M. L. (1982) in "Nucleases" (Linn, S. M., & Roberts, R. J., Eds.) pp 211–241, Cold Spring Harbor Laboratory press, Plainview, N.Y.
9. Eder, P. S. and Walder, J. A. (1991) *J. Biol. Chem.* 266, 6472–6479
10. Frank, P., Albert, S., Cazenave, C., and Toulme, J. J. (1994) *Nucleic Acids Res.* 22, 5247–5254
11. Wu, H., Lima, W. F., and Crooke, S. T. (1998) Antisense *Nucleic Acid Drug Dev.* 8, 53–61
12. Busen, W., Peters, J. H., and Hausen, P. (1977) *Eur. J. Biochem.* 74, 203–208
13. Turchi, J. J., Huang, L., Murante, R. S., Kim, Y., and Bambara, R. A. (1994) *Proc. Natl. Acad. Sci. U.S.A.* 91, 9803–9807
14. Frank, P., Braunshofer-Reiter, C., Wintersberger, U., Grimm, R., and Busen, W. (1998) *Proc. Natl. Acad. Sci. U.S.A.* 95 12872–12877
15. Cerritelli, S. M., and Crouch, R. J. (1998) *Genomics* 53, 307–311
16. Wu, H., Lima, W. L., and Crooke, S. T. (1999) *J. Biol. Chem.* 274, 28270–28278
17. Lima, W. F. and Crooke, S. T. (1997) *Biochemistry* 36, 390–398
18. Kanaya, S., Katsuda-Kakai, C., and Ikehara, M. (1991) *J. Biol. Chem.* 266, 11621–11627
19. Nakamura, H., ODA, Y., Iwai, S., Inoue, H., Ohtsuka, E., Kanaya, S., Kimura, S., Katsuda, C., Katayanagi, K., Morikawa, K., Miyashiro, H., and Ikehara, M. (1991) *Proc. Natl. Acad. Sci. U. S. A.* 88, 11535–11539
20. Katanagi, K., Miyagawa, M., Matsushima, M., Ishkiawa, M., Kanaya, S., Ikehara, M., Matsuzaki, T., and Morikawa, K. (1990) *Nature* 347, 306–309
21. Yang, W., Hendrickson, W. A., Crouch, R. J., and Satow, Y. (1990) *Science* 249, 1398–1405
22. Landt, O., Grunert, H. and Hahn, U. (1990) *Gene* 96, 125–128
23. S. A. Scaringe, F. E. Wincott and M. H. Caruthers, (1998) *J. Am. Chem. Soc.* 120, 11820–11821
24. Sambrook, J., Fritsch, E. F., and Maniatis, T. (1989) in *Molecular Cloning. A Laboratory Manual*, $2^{nd}$ sd., Cold Spring Harbor Laboratory Press, Cold Spring Harbor, N.Y.
25. Katayanagi, K., Okumura, M., and Morikawa, K. (1993) *Proteins: Struct., Funct., Genet.* 17, 337–346
26. Cerritelli, S. M. and Crouch, R. J. (1995). *RNA* 1, 246–259
27. Blyn, L. B., Swiderek, K. M., Richards, O., Stahl, D. C., Semler, B. L., and Ehrenfeld, E. (1996) *Proc. Natl. Acad. Sci. U.S.A.* 93, 11115–11120
28. Hirata, Y., Kiuchi, K., Chen, H. C., Milbrandt, J., and Guroff, G. (1993) *J. Biol. Chem.* 268, 24808–24812
29. Bamara, R. A., Murante, R. S. and Hendricksen, L. A. (1997). *J. Biol. Chem.* 272, 4647–4650
30. Dabora, J. M., Pelton, J. G., and Marqusee, S. (1996) *Biochemistry* 35, 11951–11958

What is claimed is:

1. A human RNase H1 polypeptide which comprises a mutation compared to wild type human RNase H1, wherein said mutation produces a mutant version of human RNase H1 polypeptide that consists of a deletion mutation of region I, a deletion mutation of region II, a deletion mutation of region I and region II, or a lysine-to-alanine substitution at amino acids 226 and 227 of SEQ ID NO: 3, and wherein said mutant version retains detectable cleavage activity for the RNA strand of an RNA/DNA duplex.

2. A composition comprising the human RNase H1 polypeptide of claim 1 and a pharmaceutically acceptable carrier.

3. A human H1 polypeptide which consists solely of the basic substrate binding domain which consists of region III and which retains detectable cleavage activity for the RNA strand of an RNA/DNA duplex.

4. The RNase H1 polypeptide of claim 3 which has an initial cleavage rate for the RNA strand of an RNA/DNA duplex which is at least 50% of the initial cleavage rate for a wild type human RNase H1.

5. A composition comprising the human RNase H1 polypeptide of claim 3 and a pharmaceutically acceptable carrier.

* * * * *

SEQUENCE LISTING

<160> NUMBER OF SEQ ID NOS: 4

<210> SEQ ID NO 1
<211> LENGTH: 189
<212> TYPE: PRT
<213> ORGANISM: Escherichia coli

<400> SEQUENCE: 1

Met Ser Trp Ala His Arg Val Ala Ala Ala Cys Arg Arg Gly Ser Arg
1               5                   10                  15

-continued

```
Gly Gly Met Tyr Ala Val Arg Arg Gly Lys Gly Val Trp Asn Cys
         20                  25                  30

Arg Ala Val Asp Arg Ala Arg Lys Lys Ala Asp Ala Trp Ala Val
         35                  40                  45

Arg Lys Ser Ala Ser Val Ser Gly His Asn His Gly Ser Ala Lys Ala
 50                  55                  60

Ser Lys Arg Arg Asp Gly Asp Gly His Ser Ala Tyr Ala Lys His Met
 65                  70                  75                  80

Lys Ser Val Ala Val Ser Arg Asp Ser Tyr Met Gly Asp Val Val
                 85                  90                  95

Tyr Asp Gly Cys Cys Ser Ser Asn Gly Arg Arg Arg Ala Gly Gly
                100                 105                 110

Val Tyr Trp Gly Gly His Asn Val Gly Arg Gly Arg Asn Arg Ala His
                115                 120                 125

Ala Ala Cys Lys Ala Ala Lys Asn Asn Lys Val Tyr Asp Ser Met Asn
130                 135                 140

Gly Asn Trp Val Gly Lys Lys Asn Gly Trp Lys Ser Ala Gly Lys Val
145                 150                 155                 160

Asn Lys Asp Val Ala Arg Gly Met Asp Trp Met His Val Gly His Ser
                165                 170                 175

Gly Gly Asn Ala Asp Arg Ala Arg Gly Ala Lys Ser Asp
                180                 185

<210> SEQ ID NO 2
<211> LENGTH: 17
<212> TYPE: RNA
<213> ORGANISM: Homo sapiens

<400> SEQUENCE: 2
gggcgccguc ggugugg                                                  17

<210> SEQ ID NO 3
<211> LENGTH: 286
<212> TYPE: PRT
<213> ORGANISM: Homo sapiens

<400> SEQUENCE: 3

Met Ser Trp Leu Leu Phe Leu Ala His Arg Val Ala Leu Ala Ala Leu
 1               5                  10                  15

Pro Cys Arg Arg Gly Ser Arg Gly Phe Gly Met Phe Tyr Ala Val Arg
                 20                  25                  30

Arg Gly Arg Lys Thr Gly Val Phe Leu Thr Trp Asn Glu Cys Arg Ala
                 35                  40                  45

Gln Val Asp Arg Phe Pro Ala Ala Arg Phe Lys Lys Phe Ala Thr Glu
 50                  55                  60

Asp Glu Ala Trp Ala Phe Val Arg Lys Ser Ala Ser Pro Glu Val Ser
 65                  70                  75                  80

Glu Gly His Glu Asn Gln His Gly Gln Glu Ser Glu Ala Lys Ala Ser
                 85                  90                  95

Lys Arg Leu Arg Glu Pro Leu Asp Gly Asp Gly His Glu Ser Ala Glu
                100                 105                 110

Pro Tyr Ala Lys His Met Lys Pro Ser Val Glu Pro Ala Pro Val
                115                 120                 125

Ser Arg Asp Thr Phe Ser Tyr Met Gly Asp Phe Val Val Val Tyr Thr
130                 135                 140
```

```
                            -continued

Asp Gly Cys Cys Ser Ser Asn Gly Arg Arg Arg Pro Arg Ala Gly Ile
145                 150                 155                 160

Gly Val Tyr Trp Gly Pro Gly His Pro Leu Asn Val Gly Ile Arg Leu
                165                 170                 175

Pro Gly Arg Gln Thr Asn Gln Arg Ala Glu Ile His Ala Ala Cys Lys
            180                 185                 190

Ala Ile Glu Gln Ala Lys Thr Gln Asn Ile Asn Lys Leu Val Leu Tyr
        195                 200                 205

Thr Asp Ser Met Phe Thr Ile Asn Gly Ile Thr Asn Trp Val Gln Gly
    210                 215                 220

Gln Lys Lys Asn Gly Trp Lys Thr Ser Ala Gly Lys Glu Val Ile Asn
225                 230                 235                 240

Lys Glu Asp Phe Val Ala Leu Glu Arg Leu Thr Gln Gly Met Asp Ile
                245                 250                 255

Gln Trp Met His Val Pro Gly His Ser Gly Phe Ile Gly Asn Glu Glu
            260                 265                 270

Ala Asp Arg Leu Ala Arg Glu Gly Ala Lys Gln Ser Glu Asp
            275                 280                 285

<210> SEQ ID NO 4
<211> LENGTH: 17
<212> TYPE: DNA
<213> ORGANISM: Homo sapiens

<400> SEQUENCE: 4
cccgcggcag ccacacc                                                  17
```